United States Patent
Vu

(10) Patent No.: US 7,265,547 B2
(45) Date of Patent: Sep. 4, 2007

(54) METHOD AND APPARATUS FOR ACQUIRING MR DATA WITH A SEGMENTED MULTI-SHOT RADIAL FAN BEAM ENCODING ORDER

(75) Inventor: Anthony T. Vu, Waukesha, WI (US)

(73) Assignee: General Electric Company, Schenectady, NY (US)

(*) Notice: Subject to any disclaimer, the term of this patent is extended or adjusted under 35 U.S.C. 154(b) by 126 days.

(21) Appl. No.: 11/162,621

(22) Filed: Sep. 16, 2005

(65) Prior Publication Data

US 2007/0063701 A1    Mar. 22, 2007

(51) Int. Cl.
*G01V 3/00* (2006.01)
(52) U.S. Cl. ................................. 324/309; 324/307
(58) Field of Classification Search ............... 324/309, 324/307
See application file for complete search history.

(56) References Cited

U.S. PATENT DOCUMENTS

| | | | |
|---|---|---|---|
| 4,769,603 A | | 9/1988 | Oppelt et al. |
| 6,828,788 B2* | | 12/2004 | Wang ........................ 324/309 |
| 7,030,609 B2* | | 4/2006 | Pipe ......................... 324/309 |
| 7,046,004 B2* | | 5/2006 | Bieri et al. ................. 324/307 |

OTHER PUBLICATIONS

Bieri et al., Generic Eddy-Current Compensation in Balanced Steady-State Free Procession, Proc. Intl. Soc. Mag. Reson. Med., 2004, p. 104, vol. 11.

Madhuranthakam et al., Continuously Moving Table Peripheral CE-MRA with a Radial-Elliptical Centric View Order and 2D Homodyne, Proc. Intl. Soc. Mag. Reson. Med., 2005, p. 2408, vol. 13.

Haacke et al., Physical Principal and Sequence Design, Magnetic Resonance Imaging, 1999, p. 467, 470-482, Publisher: John Wiley & Sons.

Zur et al., An Analysis of Fast Imaging Sequences with Steady-State Transverse Magnetization Refocusing, Magnetic Resonance in Medicine, 1988, pp. 175-193, vol. 6, Publisher: Academic Press, Inc.

* cited by examiner

*Primary Examiner*—Louis M. Arana
(74) *Attorney, Agent, or Firm*—Ziolkowski Patent Solutions Group, SC

(57) ABSTRACT

An MR imaging apparatus is presented and includes a plurality of gradient coils positioned about a bore of a magnet to impress a polarizing magnetic field. An RF transceiver system and an RF switch are controlled by a pulse module to transmit and receive RF signals to and from an RF coil assembly to acquire MR images. The MR imaging apparatus also includes a computer programmed to apply a 3D imaging sequence and acquire MR data using a segmented acquisition. The computer is further programmed to reconstruct an image from the MR data that is substantially free of eddy current induced artifacts.

19 Claims, 5 Drawing Sheets

METHOD AND APPARATUS FOR ACQUIRING MR DATA WITH A SEGMENTED MULTI-SHOT RADIAL FAN BEAM ENCODING ORDER

BACKGROUND OF THE INVENTION

The present invention relates generally to magnetic resonance (MR) imaging and, more particularly, to a method and apparatus for acquiring MR data with a segmented multi-shot radial fan beam encoding order. The invention further relates to reconstructing an image from the acquired MR data that is substantially free of eddy current induced artifacts.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

As is generally well-known, a number of MR imaging techniques has been developed to improve contrast between target anatomical features and background features. By improving the contrast between the target anatomical features and the background tissue, blood, etc., the diagnostic and probative value of the resulting image is also improved which facilitates more accurate, timely, and efficient diagnosis by health care providers. One such imaging technique that is widely used in cardiac applications is fully balanced steady state coherent imaging. This imaging technique (also known as b-SSFP, FIESTA, true-FISP, or b-FFE) provides high SNR per unit time and high CNR between transient signal of inflowing blood and steady-state signal of myocardial tissues, and, as such, has been exploited often for cardiac imaging. While effective for cardiac imaging, however, fully balanced steady state coherent imaging has not heretofore been applied to other clinical imaging applications. This is because the $T_2/T_1$ contrast typically achieved with such a technique does not provide clinically adequate soft tissues contrast. That is, soft tissue typically has low $T_2/T_1$ values and, as a result, conventional fully balanced steady-state coherent imaging techniques are ineffective.

While not applied with balanced steady-state coherent imaging techniques, such as b-SSFP, FIESTA, magnetization preparation techniques have been developed to improve soft tissues contrast. These magnetization preparation techniques include IR-prepared, T2-prepared, and FATSAT and they have been successfully employed with FSE, GRE, SGPR, etc. data acquisition paradigms. In order to maximize the magnetization prepared signal contrast during the acquisition of the center of k-space, a segmented centric phase ordering is generally necessary. Centric order b-SSFP acquisition, however, is sensitive to eddy current induced artifacts due to large phase encoding jumps between repetition times (TR). Moreover, these eddy current induced artifacts become more pronounced with a segmented centric phase ordering.

It would therefore be desirable to have a system and method capable of magnetization prepared contrast for fully balanced coherent imaging that reduces the change between successive phase encoding steps of a segmented acquisition to reduce the effect of eddy currents and thereby enhance the clinical feasibility of fully balanced coherent imaging to non-cardiac acquisitions.

BRIEF DESCRIPTION OF THE INVENTION

The present invention provides a system and method of acquiring MR data with a segmented acquisition that overcomes the aforementioned drawbacks.

The present invention is directed to the acquisition of MR data with a radial fan beam trajectory that is less sensitive to eddy current induced artifacts. In this regard, the present invention provides greater and more uniform centric weighting and, as a result, allows for larger segment size and shorter acquisition time. Furthermore, because data acquisition is partitioned into a number of fan beam blades or segments, the center k-space data in each segment can be exploited for motion monitoring and/or correction. Also, the present invention is applicable for cardiac, neuro, body, musculoskeletal and other imaging studies and can used with a plethora of 3D Cartesian sampling applications including, but not limited to 3D GRE, SPGR, SSFP, FSE, and the like. Moreover, the invention is applicable with gated as well as non-gated studies. In all, the present invention provides a simple and robust solution to providing improved soft tissue contrast imaging that is less prone to eddy current induced artifacts.

Therefore, in accordance with one aspect of the invention, an MR imaging apparatus includes a plurality of gradient coils positioned about a bore of a magnet to impress a polarizing magnetic field. An RF transceiver system and an RF switch are controlled by a pulse module to transmit and receive RF signals to and from an RF coil assembly to acquire MR images. The MR imaging apparatus also includes a computer programmed to apply a 3D Cartesian imaging sequence and acquire MR data using a segmented acquisition. The computer is further programmed to reconstruct an image from the MR data that is substantially free of eddy current induced artifacts.

According to another aspect, the present invention is embodied in a method that includes the step of determining polar angles for encoding steps of a 3D Cartesian acquisition with two directional phase encodings. The method further includes the steps of sorting the encoding steps based on the polar angles and grouping the encoding steps into a number of k-space blades. The method also includes the step of arranging the encoding steps for each of the number of k-space blades based on a respective distance of each encoding step from the center of k-space.

In accordance with another aspect, the invention is embodied in a computer program stored on a computer readable storage medium and having instructions which, when executed by a computer, cause the computer to define a series of encode locations for a given k-space acquisition and segment the series of encode locations into a number of k-space blades based on a respective polar angle of each encode location. The computer is also caused to arrange the encode locations of each k-space blade based on a distance of each encode location from a center of k-space. The computer is then caused to acquire k-space data for each k-space blade in an acquisition order defined by the arrangement of encode locations for the k-space blade.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
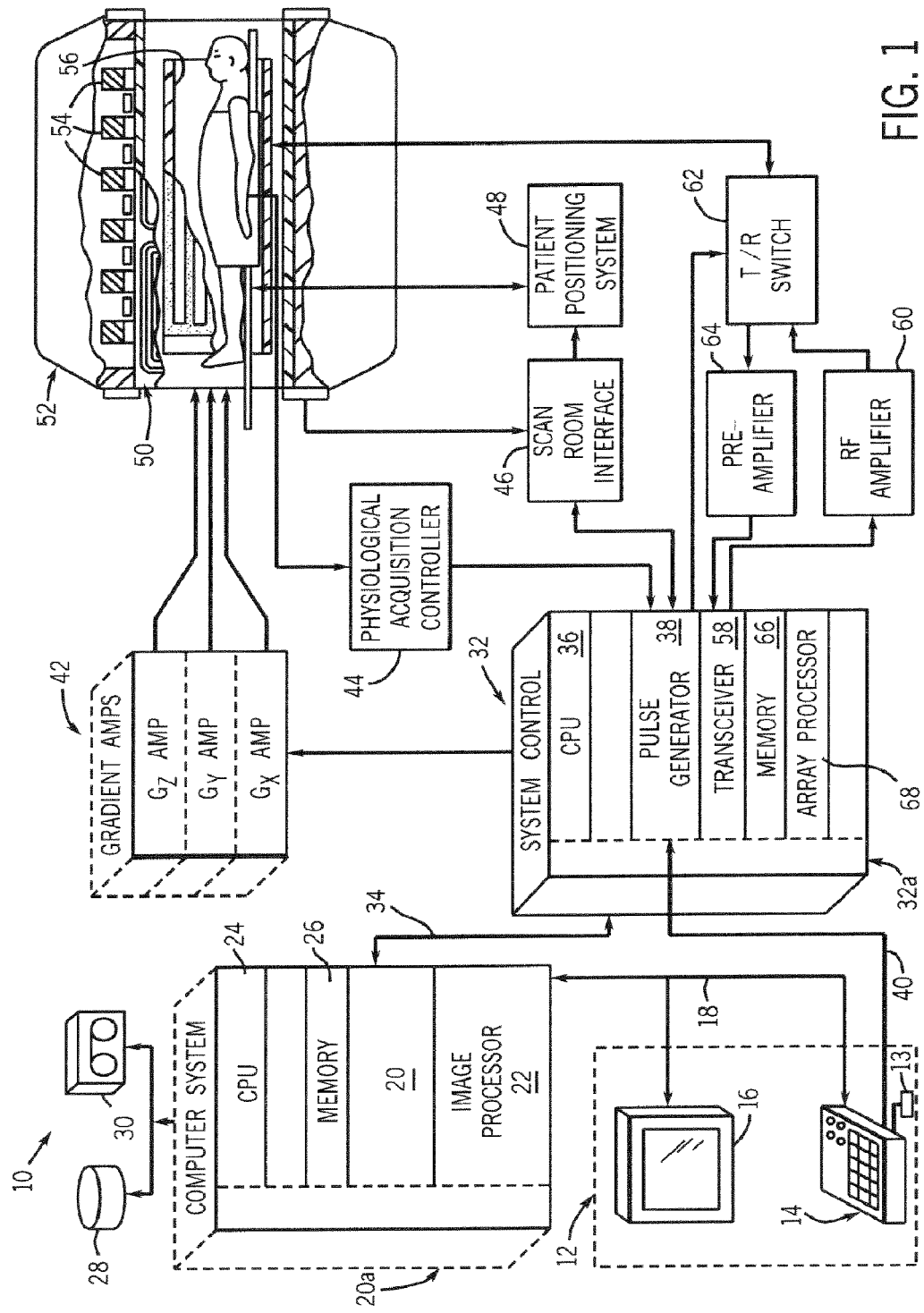
FIG. 1 is a schematic block diagram of an MR imaging system for use with the present invention.

Referring to FIG. 1, the major components of a preferred magnetic resonance (MR) imaging apparatus 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention is directed to the acquisition of MR data using a segmented multi-shot radial fan beam phase encoding order that reduces the effect of eddy currents by reducing the step-size or "jump" between successive phase encoding steps. The invention may be carried out with the MR imaging apparatus illustrated in FIG. 1, or equivalents thereof. In one preferred embodiment, the MR data is acquired according to a centric phase encoding order. It is contemplated however that other encoding orders may be implemented including, but not limited to reverse centric phase encoding, elliptical centric phase encoding, reverse elliptical centric phase encoding, and the like. The invention is particularly applicable to the acquisition of MR data with 3D Cartesian sampling where two directional phase encodings are performed.

Figure 2:
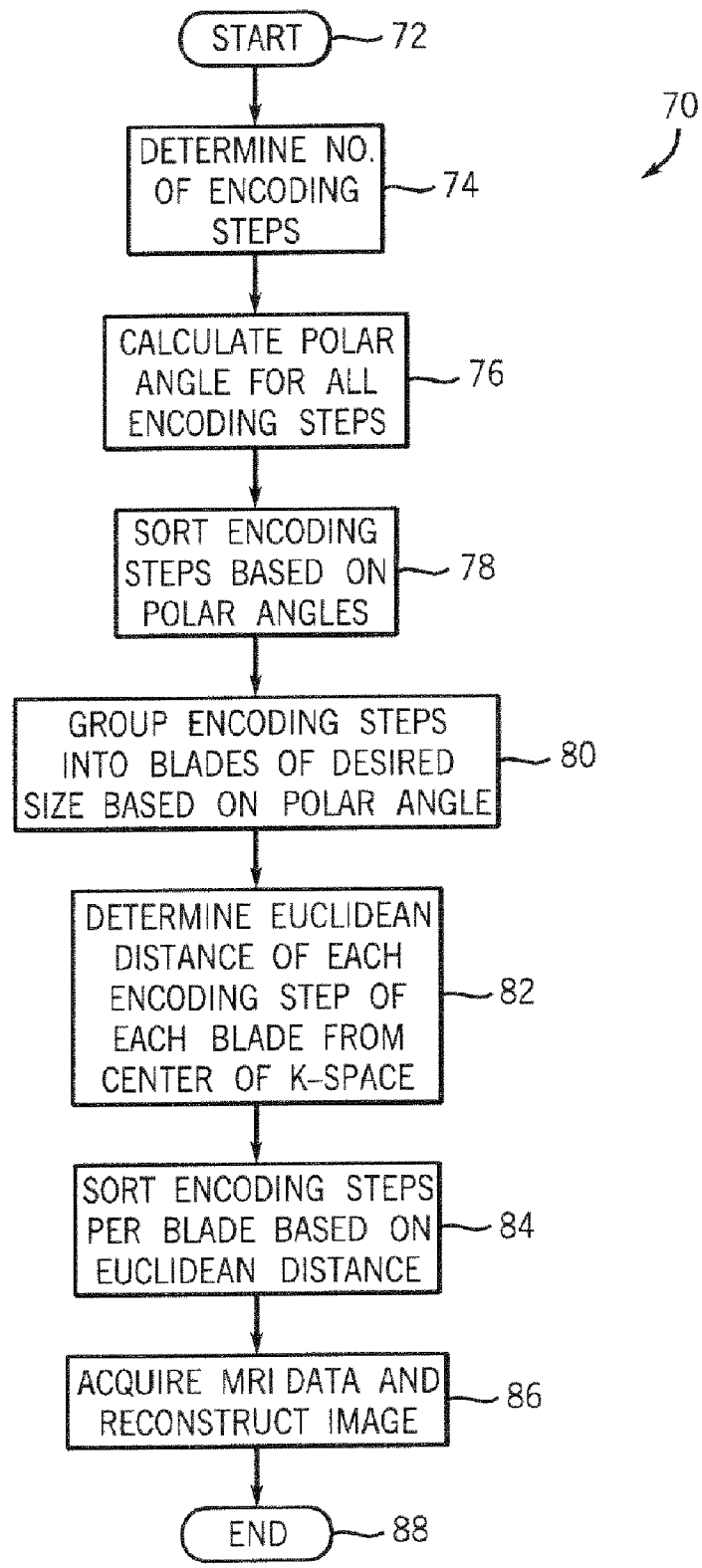
FIG. 2 is a flow chart setting forth steps of segmenting encode locations for a given k-space acquisition in accordance with the present invention.

Referring now to FIG. 2, the steps of a method for acquiring MR data with a segmented centric radial fan beam acquisition that provides true and uniform centric weighting with reduced sensitivity to eddy current effects are set forth. As will be described, the MR data is acquired without large phase encoding jumps between TRs. The method 70 begins at 72 with the prescription and preparation of an MR imaging study. This includes user-identification of various scan parameters to define the impending scan session. Based on these parameters, the method continues to determine the number of encoding steps for each k-space of the acquisition at 74. As is well-known, conventional 3D Cartesian acquisition are performed with two directional phase encodings that can be defined by a phase encoding axis ($k_y$) and a partition (or slice) encoding axis ($k_z$) on a rectangular $k_y$–$k_z$ grid. As such, each encoding step is defined by a unique $k_y,k_z$ location or position in k-space. The method then calculates or otherwise determines 76 the polar angle, θ, in radians (0–2π) or in degrees (0–360°) for all encoding steps ($k_z,k_y$) of each k-space relative to the $k_z$ axis, where θ=arctan ($k_y/k_z$) or arctan ($k_z/k_y$). The encoding steps, now defined by variables $k_z,k_y$,θ are then sorted 78 in either ascending or descending order based on the respective polar angles, θ.

The polar angle arranged encoding steps are then grouped at 80 into fan beam or k-space blades of desired size based on their respective polar angles. The desired size of each k-space blade corresponds to the number of phase encoding steps per blade. While it is preferred that each k-space blade have the same size or number of phase encoding steps, it is contemplated that one or more k-space blades may have more encoding steps than the other k-space blades.

After the encoding steps have been segmented into respective k-space blades, the encoding steps of each blade or segment of each k-space are arranged based on their Euclidian distance from the center of k-space. Accordingly, at 82, the process determines the Euclidian distance of each encoding step from the center of k-space. The distance from the center of k-space for each encoding step ($k_y,k_z$) is calculated from $(k_y^2+k_z^2)^{1/2}$. Using the distance from the center of k-space as an index, the encoding steps of each k-space blade are then arranged at 84 in ascending order. With the k-space now segmented into a number of k-space blades and the encoding steps of each k-space blade arranged based on the distance of each encoding step from the center of k-space, method 70 continues to the acquisition of MR data, and the sampling of k-space and image reconstruction 86. In this regard, k-space is sampled on a per blade or segment basis and, preferably, with a centric order acquisition. Thus, k-space is traversed on a per segment basis from point closest to the center (origin) of k-space, i.e., lowest phase encoding gradient value, to the points farthest from the center of k-space. Accordingly, the distance between each phase encoding step is significantly reduced relative to conventional segmented centric acquisitions and, as a result, the effect of eddy currents is reduced and an image substantially devoid of eddy current induced artifacts can be reconstructed. The method ends at 88 following image reconstruction.

Figure 3:
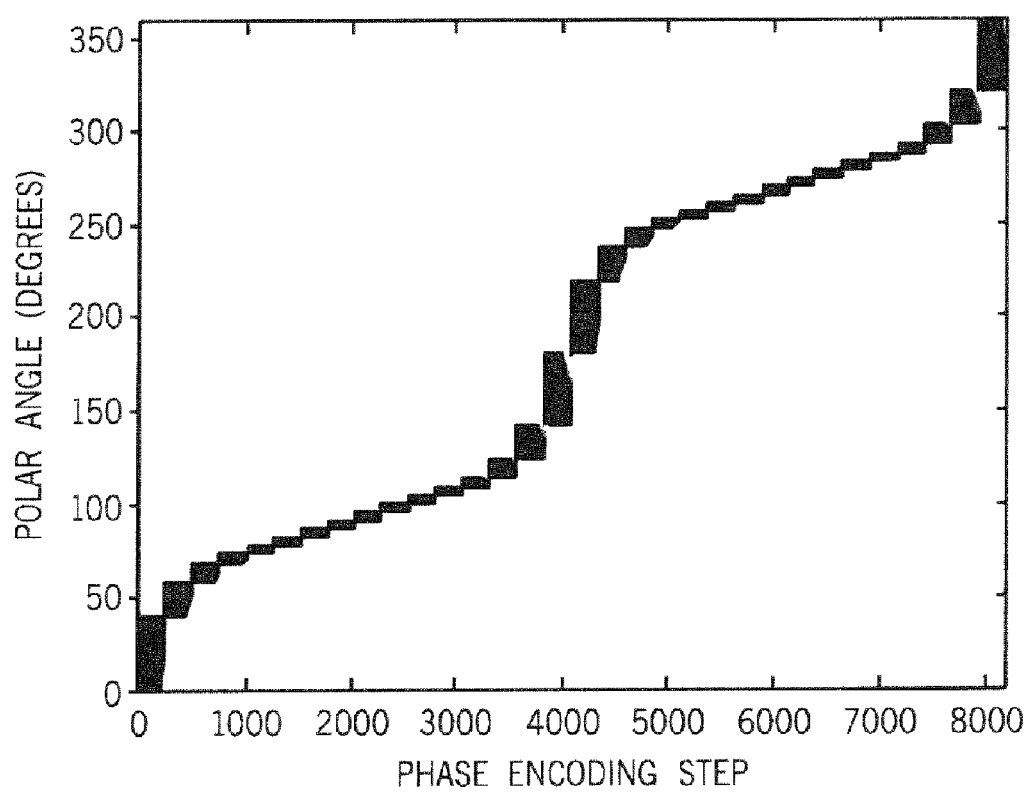
FIG. 3 illustrates distribution of the polar angles of the encoding steps of a given k-space after sorted in ascending order manner.

Referring now to FIG. 3, an exemplary polar angle distribution (sorted using ascending order) is illustrated for an acquisition consisting of 8192 phase encoding steps divided into 32 separate k-space blades or segments with 256 steps per k-space blade. One skilled in the art will appreciate that the angular coverage for each k-space segment may be different for typical Cartesian coverage due to smaller number of partition encoding steps.

Figure 4:
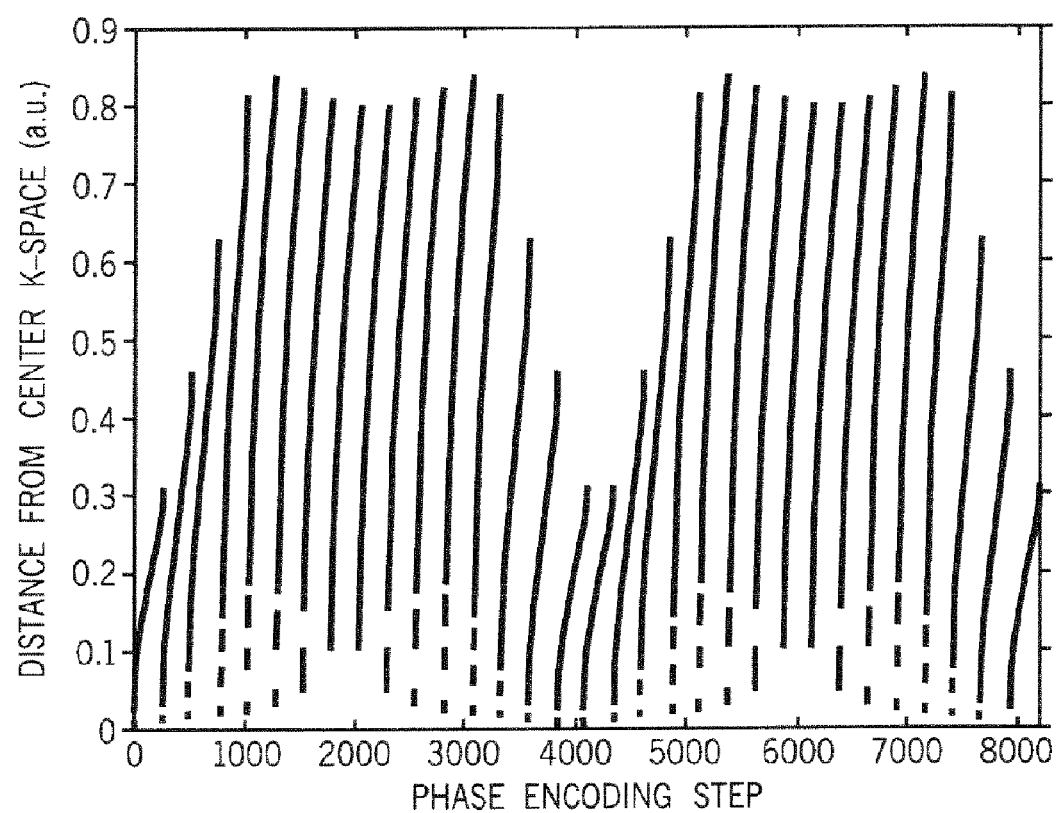
FIG. 4 illustrates distribution of the given k-space based on the Euclidian distance of each encoding step from the center of the given k-space.

Referring now to FIG. 4, Euclidian distance from center of k-space distribution is shown for an acquisition consisting of 8192 phase encoding steps divided into 32 segments with 256 steps per segment. In the illustrated distribution, the encoding steps for each segment were sorted in ascending order based on their Euclidian distance from the center (origin) of k-space.

Figure 5:
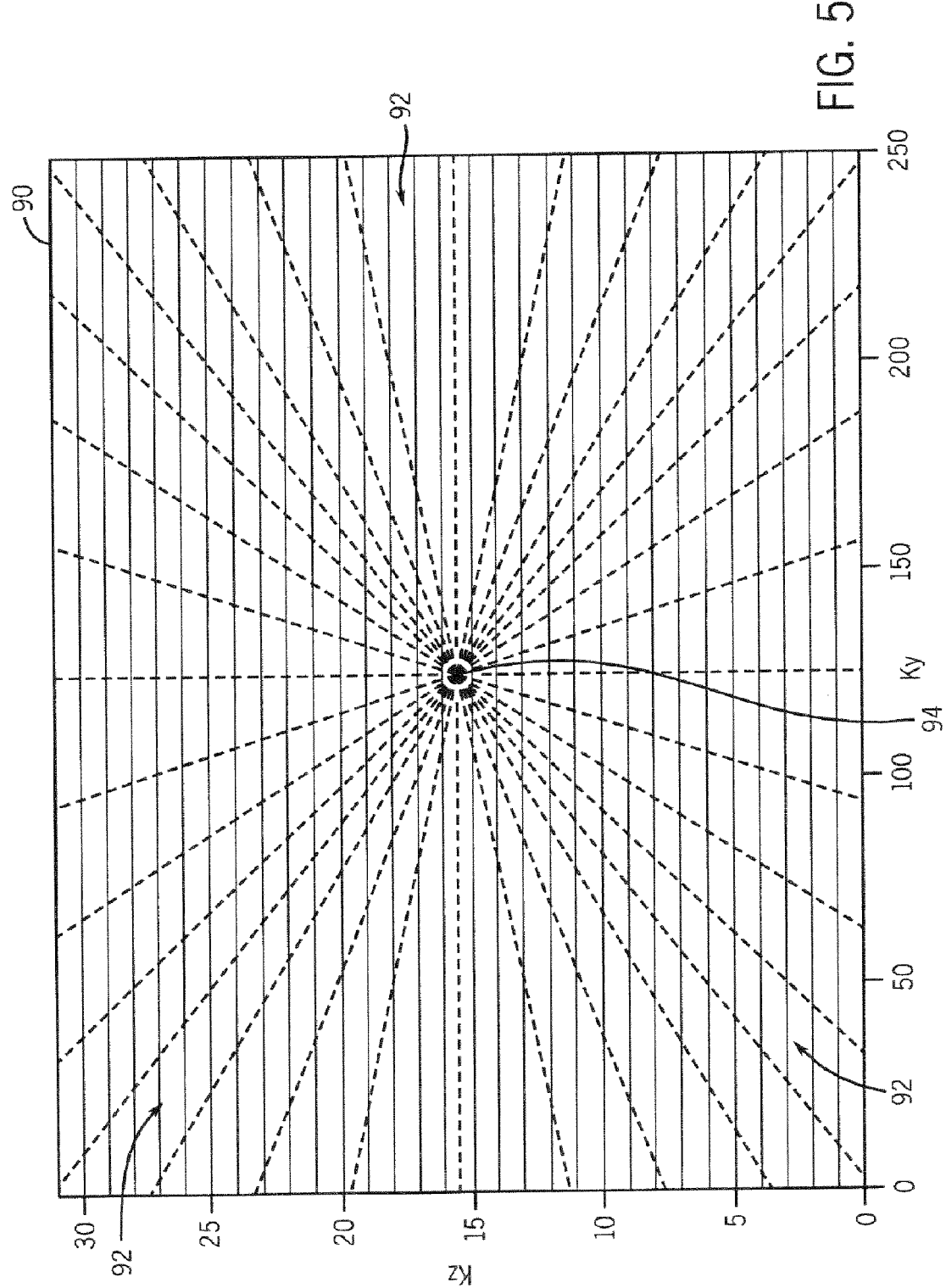
FIG. 5 is a schematic representation of the given k-space arranged into several radial fan beam k-space blades in accordance with the present invention.

FIG. 5 illustrates an exemplary radial fan beam segmentation 90 of an acquisition consisting of 8192 phase encoding steps. The segment or k-space blade size was selected to have 256 encoding steps thereby resulting in thirty-two segments or k-space blades 92. As illustrated, each k-space blade 92 extends from the center 94 of k-space 90. As described above, for centric ordering acquisition, k-space 90 is traversed on a per blade basis from the point closest to the center of k-space to the points farthest from the center of k-space. For a reverse centric ordering acquisition, k-space is traversed on a per blade basis from the point farthest from the center of k-space to the points closest to the center of k-space. It is contemplated that each k-space blade can be traversed sequentially, randomly, or in an interleaved manner.

As described herein, the present invention provides a radial fan beam trajectory for true centric k-space sampling that is robust, efficient, and less sensitive to eddy current induced artifacts. The radial fan beam phase encoding order achieves uniform centric weighting that permits application of larger segments (blades) thereby reducing scan time and increasing subject throughput relative to conventional segmented centric acquisition. The invention is applicable to a number of 3D Cartesian sampling acquisitions including, but not limited to 3D GRE, SPGR, SSFP, b-SSFP, FSE, and the like. The invention may be applied for a number of imaging studies including, but not limited to neuro imaging and axial C-spine imaging. The invention is also applicable with FATSAT and/or $T_1/T_2$-prepared segmented radial fan beam acquisitions using a fully balanced (or unbalanced) coherent (or incoherent) imaging pulse sequence. Further, the invention is believed to be applicable for FATSAT segmented radial fan beam acquisitions with fully balanced coherent imaging sequences for high-resolution musculoskeletal anatomical and non-contrast MR angiography studies. The MR data close to center of k-space may also be used for general motion monitoring and/or correction. The invention is also applicable with physiologically gated and non-gated acquisitions, dedicated and non-dedicated magnetization preparation sequences, and imaging techniques with or without dedicated recovery periods.

Therefore, an MR imaging apparatus is presented and includes a plurality of gradient coils positioned about a bore of a magnet to impress a polarizing magnetic field. An RF transceiver system and an RF switch are controlled by a pulse module to transmit and receive RF signals to and from an RF coil assembly to acquire MR images. The MR imaging apparatus also includes a computer programmed to apply a 3D imaging sequence and acquire MR data using a segmented acquisition. The computer is further programmed to reconstruct an image from the MR data that is substantially free of eddy current induced artifacts.

The present invention is also embodied in a method that includes the step of determining polar angles for encoding steps of a k-space acquisition. The method further includes the steps of sorting the encoding steps based on the polar angles and grouping the encoding steps into a number of k-space blades. The method also includes the step of arranging the encoding steps for each of the number of k-space blades based on a respective distance of each encoding step from the center of k-space.

The invention is also embodied in a computer program stored on a computer readable storage medium and having instructions which, when executed by a computer, cause the computer to define a series of encode locations for a given k-space acquisition and segment the series of encode locations into a number of k-space blades based on a respective polar angle of each encode location. The computer is also caused to arrange the encode locations of each k-space blade based on a distance of each encode location from a center of k-space. The computer is then caused to acquire k-space data for each k-space blade in an acquisition order defined by the arrangement of encode locations for the k-space blade.

The present invention has been described in terms of the preferred embodiment, and it is recognized that equivalents, alternatives, and modifications, aside from those expressly stated, are possible and within the scope of the appending claims.

What is claimed is:

1. An MR imaging apparatus comprising:
  a plurality of gradient coils positioned about a bore of a magnet to impress a polarizing magnetic field and an RF transceiver system and an RF switch controlled by a pulse module to transmit RF signals to an RF coil assembly to acquire MR images; and
  a computer readable storage medium having stored thereon a computer program comprising instructions which when executed by a computer cause the computer to:
    apply a 3D imaging sequence for MR data acquisition;
    define a segmented acquisition according to a series of radial fan beams extending from a center of k-space;
    acquire MR data using the segmented acquisition for a number of encode locations based on a respective distance of each encode location from the center of k-space; and
    reconstruct an image from the MR data that is substantially free of eddy current induced artifacts.

2. The MR imaging apparatus of claim 1 wherein the computer is further programmed to:
  calculate a polar angle of each encode location of k-space;
  sort the encode locations in one of an ascending order or a descending order based on the polar angles;
  group the encode locations into radial fan blades of a desired size; and
  arrange the encode locations of each radial fan blade in ascending order based on a distance of each encode location from the center of k-space.

3. The MR imaging apparatus of claim 2 wherein the computer is further programmed to determine a Euclidean distance of each encode location of a radial fan blade from the center of k-space.

4. The MR imaging apparatus of claim 1 wherein the computer is further programmed to acquire the MR data in a segmented centric radial fan beam acquisition.

5. The MR imaging apparatus of claim 1 wherein the computer is further programmed to acquire the MR data in a segmented reverse centric radial fan beam acquisition.

6. The MR imaging apparatus of claim 1 wherein the computer is further programmed to acquire MR data for each radial fan beam in one of a sequential, a random, or interleaved order.

7. The MR imaging apparatus of claim 1 wherein the computer is further programmed to acquire the MR data with a 3D Cartesian sampling acquisition.

8. The MR imaging apparatus of claim 7 wherein the 3D Cartesian sampling acquisition is one of a 3D GRE, a SPGR, a SSFP, a b-SSFP, an EPI and a FSE acquisition.

9. A method comprising the steps of:
  determining polar angles for encoding steps of a k-space acquisition;
  sorting the encoding steps based on the polar angles;
  grouping the encoding steps into a number of k-space blades; and
  arranging the encoding steps for each of the number of k-space blades based on a respective distance of each encoding step from a center of k-space.

10. The method of claim 9 further comprising the step of acquiring each k-space blade in one of a centric order or a reverse centric order.

11. The method of claim 9 further comprising the step of sorting the encoding steps in either a descending order or an ascending order based on polar angle.

12. The method of claim 9 further comprising the step of arranging the encoding steps of each grouping in an ascending order.

13. The method of claim 9 wherein the distance is Euclidean distance.

14. A computer readable storage medium having a computer program stored thereon and representing a set of instructions that when executed by a computer causes the computer to:
  define a series of encode locations for a given k-space acquisition;
  segment the series of encode locations into a number of k-space blades based on a respective polar angle of each encode location;
  arrange the encode locations of each k-space blade based on a distance of each encode location from a center of k-space; and
  acquire k-space data for each k-space blade in an acquisition order defined by the arrangement of encode locations for the k-space blade.

15. The computer readable storage medium of claim 14 wherein the set of instructions further causes the computer to arrange the encode locations of each k-space blade in ascending order based on the distance of each encode location from the center of k-space.

16. The computer readable storage medium of claim 14 wherein the set of instructions further causes the computer to reconstruct an image substantially free of eddy current induced artifacts from the k-space data.

17. The computer readable storage medium of claim 14 wherein the set of instructions further causes the computer to sort the series of encode locations in either a descending order or an ascending order based on polar angle.

18. The computer readable storage medium of claim 14 wherein the set of instructions further causes the computer to acquire the k-space data for each k-space blade in either a centric acquisition order or a reverse centric acquisition order.

19. The computer readable storage medium of claim 14 wherein the set of instructions further causes the computer to determine the distance of each encode location from the center of k-space from a Euclidean distance of each encode location from the center of k-space.

* * * * *